US007875610B2

(12) United States Patent
Szalai et al.

(10) Patent No.: US 7,875,610 B2
(45) Date of Patent: Jan. 25, 2011

(54) PYRIMIDINYL-PIPERAZINES USEFUL AS $D_3/D_2$ RECEPTOR LIGANDS

(75) Inventors: Gizella Bartane Szalai, Budapest (HU); Eva Againe Csongor, Budapest (HU); Gyorgy Domany, Obanya (HU); Istvan Gyertyan, Budapest (HU); Bela Kiss, Budapest (HU); Judit Laszy, Nagykovacsi (HU); Katalin Saghy, Budapest (HU); Eva Schmidt, Budapest (HU); Sandor Farkas, Budapest (HU); Zsolt Komlodi, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 0 days.

(21) Appl. No.: 12/327,180

(22) Filed: Dec. 3, 2008

(65) Prior Publication Data

US 2009/0143398 A1 Jun. 4, 2009

Related U.S. Application Data

(60) Provisional application No. 60/991,913, filed on Dec. 3, 2007.

(51) Int. Cl.
C07D 239/48 (2006.01)
A61K 31/506 (2006.01)

(52) U.S. Cl. ............... 514/235.8; 514/252.14; 544/122; 544/295

(58) Field of Classification Search ............... 544/122, 544/295; 514/235.8, 252.14
See application file for complete search history.

(56) References Cited

U.S. PATENT DOCUMENTS

| 4,957,921 A | 9/1990 | Caprathe et al. |
| 6,919,342 B2 | 7/2005 | Haupt |

FOREIGN PATENT DOCUMENTS

| EP | 0 431 580 | 3/1995 |
| WO | WO 99/67206 | 12/1999 |

OTHER PUBLICATIONS

Ulrich, Chapter 4: Crystallization, Kirk-Othmer Encyclopedia of Chemical Technology, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Le Foll, et al., PubMed Abstract (Expert Opin Investig Drugs, 16(1):45-57), Jan. 2007.*
Layzer, Degenerative Diseases of the Nervous System, Cecil Textbook of Medicine, 20th Edition, vol. 2, pp. 2050-2057, 1996.*
Damasio, Alzheimer's Disease and Related Dementias, Cecil Textbook of Medicine, 20th Edition, vol. 2, pp. 1992-1996, 1996.*
Schwartz et al., Possible implications of the dopamine D3 receptor in schizophrenia and in antipsychotic drug actions, Brain Research Reviews 31 (2000) pp. 277-287.*
Bézard et al., "Attenuation of levodopa-induced dyskinesia by normalizing dopamine D3 receptor function," Nat. Med., 2003, 9(6):762-767.
Brunton et al. (eds.), Goodman and Gilman's The Pharmacological Basis of Therapeutics, 2005, 11th Edition, McGraw Hill, p. 462.
Creese et al., "Species variation in dopamine receptor binding," Eur. J. Pharmacol., 1979, 60:55-66.
Greengrass and Bremner, "Binding characteristics of 3H-prazosin to rat brain alpha-adrenergic receptors," Eur. J. Pharmacol., 1979, 55(3):323-326.
Guérémy et al., "2-Amino-6-chloro-4-(N-methylpiperazino)pyrimidines, inhibitors of spiroperidol binding," J. Med. Chem., 1982, 25(12):1459-1465.
Heidbreder et al., "The role of central dopamine D3 receptors in drug addiction: a review of pharmacological evidence," Brain Res. Rev., 2005, 49:77-105.
Joyce, "Dopamine D3 receptor as a therapeutic target for antipsychotic and antiparkinsonian drugs," Pharmacol. Therap., 2001, 90:231-259.
Laszy et al., "Dopamine D3 receptor antagonists improve the learning performance in memory-impaired rats," Psychopharmacol., 2005, 179(3):567-575.
Levant, "The D3 dopamine receptor: neurobiology and potential clinical relevance," Pharmacol. Rev., 1997, 49(3):231-252.
Levant et al., CNS Drugs, 1999, 12:391.
Levant and McCarson, "D(3) dopamine receptors in rat spinal cord: implications for sensory and motor function," Neurosci. Lett., 2001, 303:9-12.

(Continued)

Primary Examiner—Deepak Rao
(74) Attorney, Agent, or Firm—Fish & Richardson P.C.

(57) ABSTRACT

The present invention relates to new dopamine $D_3$ and $D_2$ ligands of formula (I):

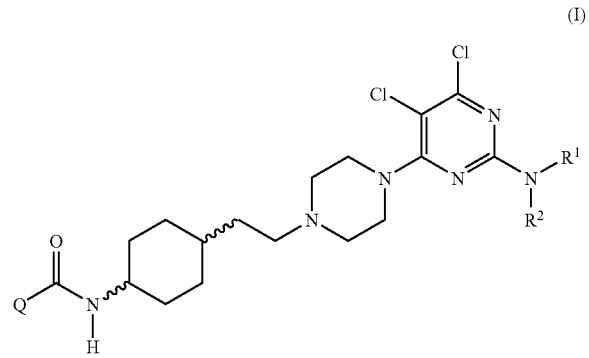

wherein R1, R2 and Q are as described herein, and/or geometric isomers and/or stereoisomers and/or diastereomers and/or salts and/or hydrates and/or solvates and/or polymorphs thereof. The invention also relates to processes for preparing the same, to compositions containing the same and to their use in the treatment and/or prevention of conditions which requires modulation of dopamine receptors.

9 Claims, No Drawings

OTHER PUBLICATIONS

Pacher and Kecskeméti, "Cardiovascular side effects of new antidepressants and antipsychotics: new drugs, old concerns?" *Curr. Pharm. Des.*, 2004, 10(20):2463-2475.

Pilla et al., "Selective inhibition of cocaine-seeking behaviour by a partial dopamine D3 receptor agonist," *Nature*, 1999, 400:371-375.

Schwartz et al., "Dopamine D3 receptor: basic and clinical aspects," *Clin. Neuropharmacol.*, 1993, 16(4):295-314.

Schwartz et al., "Possible implications of the dopamine D(3) receptor in schizophrenia and in antipsychotic drug actions," *Brain Res. Rev.*, 2000, 31:277-287.

Sokoloff et al., "Molecular cloning and characterization of a novel dopamine receptor (D3) as a target for neuroleptics," *Nature*, 1990, 347:146-151.

Stahl, *Essential Psychopharmacology. Neuroscientific Basis and Practical Applications*, 2000, 2nd ed., p. 409, Cambridge University Press.

Stemp et al., "Design and synthesis of trans-N-[4-[2-(6-cyano-1,2,3,4-tetrahydroisoquinolin-2-yl)ethyl]cyclohexyl]-4-quinolinecarboxamide (SB-277011): A potent and selective dopamine D(3) receptor antagonist with high oral bioavailability and CNS penetration in the rat," *J. Med. Chem.*, 2000, 43(9):1878-1885.

Wong and Van Tol, "Schizophrenia: from phenomenology to neurobiology," *Neurosci. Biobehav. Rev.*, 2003, 27(3):269-306.

http://www.fda.gov/medwatch/safety/2006/Sep_PIs/RisperdalConsta_PI.pdf.

http://www.fda.gov/medwatch/safety/2006/Aug_PIs/Zyprexa_PI.pdf.

Aiken, C., "Pramipexole in psychiatry. A systematic review of literature," *J. Clin Psychiatry.* 68:1230-1237, 2007.

Burger's Medicinal Chemistry and Drug Discovery. vol. 1. Drug Discovery, 6th Edition. Wiley Interscience. Ed. Donald J. Abraham, ISBN 978-0-471-27090-4, Jan. 2003).

Di. Chiara, G., "Drug addiction as dopamine-dependent associative learning disorder," 1999. *Eur. J. Pharmacol.* 375: 13-30.

Maj, J. et al, "Effect of antidepressant drugs administered repeatedly on the dopamine D3 receptors in the rat brain," *Eur. J. Pharmacol.* 351:31-37, 1998.

Millan, M.J., Gressier, H., Brocco, M., 1997. "The dopamine D3 receptor antagonist, (+)-S 14297, blocks the cataleptic properties of haloperidol in rats," *Eur. J. Pharmacol.* 321, R7-R9.

Papp, M., Wieronska, J., "Antidepressant-like activity of amisulpride in two animal models of depression," *J. Psychopharmacol*, 14:46-52, 2000.

Russel, V.A., "Neurobiology of animal models of attention-deficit hyperactivity disorder," *J. Neurosci. Methods* 161:185-198, 2007.

Rogóz Z, Klodzińska A, Maj J. "Anxiolytic-like effect of nafadotride and PNU 99194A, dopamine D3 receptor antagonists in animal models," *Pol J Pharmacol*. Nov.-Dec. 2000;52(6):459-62.

P. Seeman, "Brain dopamine receptors" *Pharmacological Review*, vol. 32 No. 3 1980, pp. 238.

Shalev U, Grimm JW, Shaham Y, 2002. "Neurobiology of relapse to heroin and cocaine seeking: a review.," *Pharmacol. Rev.* 54 (1), 1-42.

Steiner H, Fuchs S, Accili D "D3 dopamine receptor-deficient mouse: evidence for reduced anxiety," *Physiol Behav*. Dec. 31, 1997;63(1):137-41.

Thanos, P.K. et al., "The effects of two highly selective dopamine D3 receptor antagonists (SB-277011A and NGB-2904) on food selfadministration in a rodent model of obesity," *Pharmacol Biochem Behav.* 89: 499-507, 2008.

van der Kooij, M.A, Glennon, J.C. "Animal models concerning the role of dopamine in attention-deficit hyperactivity disorder," *Neuroscience and Biobehavioral Reviews* 31: 597-618, 2007.

Tada et al., "Combined treatment of quetiapine with haloperidol in animal models of antipsychotic effect and extrapyramidal side effects: comparison with risperidone and chlorpromazine," *Psychopharmacology (Berl)*, Oct. 2004, vol. 176(1); pp. 94-100.

Paul Willner, P. Anthony S. Hale, A.S. and Argyropoulos, S. "Dopaminergic mechanism of antidepressant action in depressed patients," *J. Affective Disorders* 86: 37-45, 2005.

Gyertyan, I. et al, "Effects of dopamine $D_3$ receptor antagonists on spontaneous and agonist-reduced motor activity in NMRI mice and Wistar rats: comparative study with nafadotride, U 99194A and SB 277011," *Behavioural Phramacology*, vol. 15(4), 2004, pp. 253-262.

Gyertyan, I. et al., "The selective dopamine D3 receptor antagonists, SB 277011-A and S 33084 block haloperidol-induced catalepsy in rats," *Euro. Jour. of Pharmacology*, vol. 572, 2007, pp. 171-174.

\* cited by examiner

PYRIMIDINYL-PIPERAZINES USEFUL AS D₃/D₂ RECEPTOR LIGANDS

CROSS REFERENCE TO RELATED APPLICATIONS

This application claims priority under 35 U.S.C. §119(e) of U.S. provisional application Ser. No. 60/991,913, filed Dec. 3, 2007.

FIELD OF THE INVENTION

The present invention relates to new dopamine $D_3$ and $D_2$ receptor subtype preferring ligands of formula (I) and/or geometric isomers and/or stereoisomers and/or diastereomers and/or salts and/or hydrates and/or solvates and/or polymorphs thereof. The invention also relates to processes for preparing the same, to compositions containing the same and to their use in the treatment and/or prevention of conditions which requires modulation of dopamine receptors.

BACKGROUND OF THE INVENTION

Cyclohexane derivatives that are useful as therapeutics for the treatment of pain are described in International Patent Publication No. WO 99/67206.

Compounds containing a cyclohexane, pyrimidine and piperazine ring are described in European Patent No. EP 431,580 and U.S. Pat. No. 4,957,921. These compounds act as central nervous system agents and dopaminergic agents, respectively. These compounds, however, do not contain an alkyl-amino group in the 2-position of the pyrimidine ring. Dopamine $D_3$ receptor modulator compounds containing a pyrimidine and piperazine ring are described in U.S. Patent Application Publication No. 2004/259882. These compounds do not, however, contain a cyclohexane ring.

2-Amino-6-chloro-4-(N-methylpiperazino)pyrimidines as inhibitors of spiroperidol binding are described in, e.g., *J. Med. Chem.*, 25, 1459, (1982).

SUMMARY OF THE INVENTION

Surprisingly, it has been found that in contrast to the compounds described above, the compounds of formula (I) of the present invention have high or very high affinity for dopamine $D_3$ receptors, and moderate to high affinity for dopamine $D_2$ receptors always in such a combination that the $D_3$ affinity is 5 to 50 fold higher than the $D_2$ affinity. In addition, the compounds of the present invention show even higher selectivity over other receptors. For example, these compounds do not show affinity for alpha-1 adrenoceptors, i.e., their inhibitor constants (Ki) are higher or much higher than 1000 nM.

The dual (i.e. $D_3$ and $D_2$) receptor functional antagonism coupled in the above mentioned particular proportion is especially important as it allows the simultaneous manifestation of the beneficial modulation of both $D_3$ and $D_2$ receptors, however, without the appearance of the known disadvantages of each individual receptor action.

The compounds of formula (I) will be referred to in this application as "$D_3/D_2$ ligands".

The present invention relates to new piperazine derivatives of formula (I):

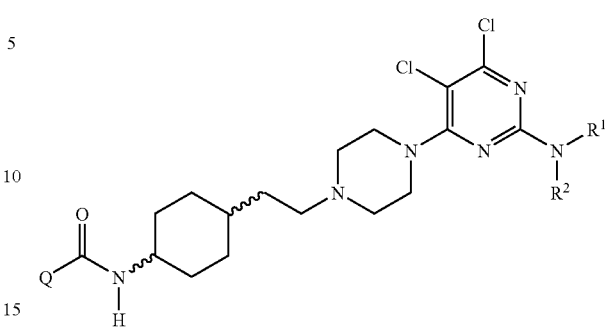

wherein
Q represents $C_{1-4}$ alkyl, —$NR^3R^4$, phenyl, optionally substituted phenyl, 1-pyrrolidinyl, 1-piperidinyl, 4-$R^5$-piperazin-1-yl or 4-morpholinyl group;
$R^1$ represents hydrogen or $C_{1-4}$ alkyl group;
$R^2$ represents hydrogen or $C_{1-4}$ alkyl group;
$R^3$ represents hydrogen, $C_{1-4}$ alkyl group, phenyl or optionally substituted phenyl;
$R^4$ represents hydrogen, $C_{1-4}$ alkyl group, phenyl or optionally substituted phenyl;
$R^5$ represents hydrogen or $C_{1-4}$ alkyl group;

and/or geometric isomers and/or stereoisomers and/or diastereomers and/or salts and/or hydrates and/or solvates and/or polymorphs thereof, to processes for preparing the same, to pharmacological compositions containing the same and to their use in the treatment and/or prevention of pathological conditions which require the modulation of dopamine receptors, such as, but not limited to, psychoses (e.g. schizophrenia, schizo-affective disorders), drug (e.g. alcohol, cocaine, nicotine, opioids) abuse, cognitive impairment accompanying schizophrenia, mild-to-moderate cognitive deficits, dementia, psychotic states associated with dementia, eating disorders (e.g. bulimia nervosa, etc.), attention deficit disorders, hyperactivity disorders, psychotic depression, mania, bipolar disorder, paranoid and delusional disorders, dyskinetic disorders (e.g. Parkinson's disease, neuroleptic induced parkinsonism, tardive dyskinesia), depression and depressive states, anxiety disorders, sexual dysfunctions (eg. erectile dysfunctions), sleep disorders, emesis, aggression, autism and pain.

The present invention also relates to compounds of formula (III):

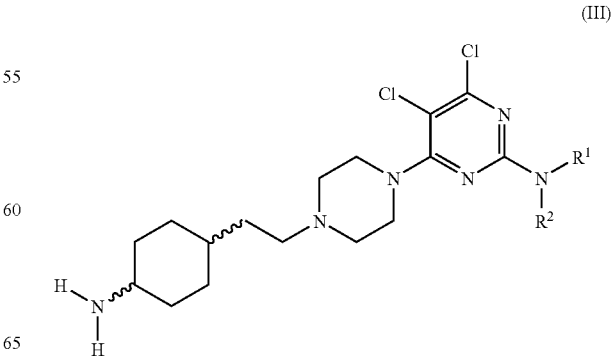

wherein
R¹ represents hydrogen or $C_{1-4}$ alkyl group, and
R² represents hydrogen or $C_{1-4}$ alkyl group.

DETAILED DESCRIPTION OF THE INVENTION

In one aspect, the present invention relates to compounds of formula (I):

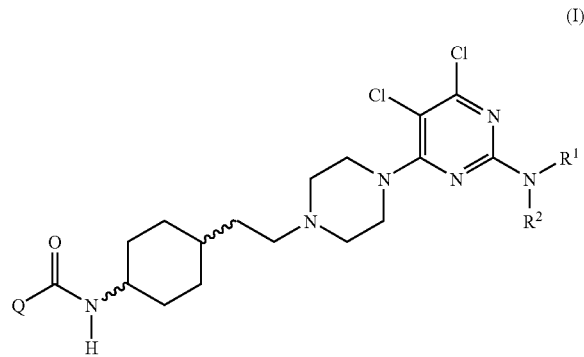

(I)

wherein
Q represents $C_{1-4}$ alkyl, —NR³R⁴, phenyl, optionally substituted phenyl, 1-pyrrolidinyl, 1-piperidinyl, 4-R⁵-piperazin-1-yl or 4-morpholinyl group;
R¹ represents hydrogen or $C_{1-4}$ alkyl group;
R² represents hydrogen or $C_{1-4}$ alkyl group;
R³ represents hydrogen, $C_{1-4}$ alkyl group, phenyl or optionally substituted phenyl;
R⁴ represents hydrogen, $C_{1-4}$ alkyl group, phenyl or optionally substituted phenyl;
R⁵ represents hydrogen or $C_{1-4}$ alkyl group;

and/or geometric isomers and/or stereoisomers and/or diastereomers and/or pharmaceutically acceptable salts and/or hydrates and/or solvates and/or polymorphs thereof.

The term "optionally substituted phenyl" as used herein means a phenyl group which can be substituted in any position by one or more halogen, $C_{1-4}$ alkyl, $C_{1-4}$ alkoxy, trifluoromethyl and/or cyano group, or combinations thereof.

The present invention also relates to salts of compounds of formula (I) formed with acids.

Both organic and inorganic acids can be used for the formation of acid addition salts. Suitable inorganic acids include, but are not limited to, hydrochloric acid, sulfuric acid, nitric acid and phosphoric acid. Representatives of monovalent organic acids include, but are not limited to, formic acid, acetic acid, propionic acid, and different butyric acids, valeric acids and capric acids. Representatives of bivalent organic acids include, but are not limited to, oxalic acid, malonic acid, maleic acid, fumaric acid and succinic acid. Other organic acids can also be used, such as hydroxy acids, for example, citric acid, tartaric acid, or aromatic carboxylic acids, for example, benzoic acid or salicylic acid, as well as aliphatic and aromatic sulfonic acids, for example, methanesulfonic acid, naphtalenesulfonic acid and p-toluenesulfonic acid. A preferred group of acid addition salts are those in which the acid component itself is physiologically acceptable and does not have a therapeutic effect in the applied dose and/or it does not have unfavourable influence on the effect of the active ingredient. These acid addition salts are pharmaceutically acceptable acid addition salts. Acid addition salts which are not pharmaceutically acceptable acid addition salts can be advantageous in the purification and isolation of the desired compounds of formula (I), and are therefore also included within the scope of the present invention.

Solvates and/or hydrates of compounds of formula (I), as well as solvates and/or hydrates of salts of compounds of formula (I) are also included within the scope of the present invention.

One of ordinary skill in the art will recognize that compounds of Formula I can exist in different tautomeric and geometrical isomeric forms. For example, the compounds of formula (I) exist in the form of cis and trans isomers with respect to the configuration of the cyclohexane ring. The compounds of present invention are preferably in the trans configuration. In addition, certain compounds of formula (I) can exist as stereoisomers and diastereomers. All of these compounds, including cis isomers, trans isomers, diastereomic mixtures, racemates, nonracemic mixtures of enantiomers, substantially pure, and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of formulas (I) can likewise be obtained by utilizing optically active starting materials in chiral synthesis processes under reaction conditions which do not cause racemization.

One of ordinary skill in the art will also recognize that some of the compounds of formula (I) can exist in different polymorphic forms. As known in the art, polymorphism is an ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

As used herein in the present specification and claims a "compound of formula (I)" will be deemed to encompass both the free base and salts, e.g., pharmaceutically acceptable salts, thereof.

In certain embodiments, preferred compounds of the invention are those compounds of formula (I) wherein
Q represents $C_{1-4}$ alkyl, NR³R⁴ or 4-morpholinyl group,
R¹ represents hydrogen or $C_{1-4}$ alkyl group;
R² represents hydrogen or $C_{1-4}$ alkyl group;
R³ represents hydrogen or $C_{1-4}$ alkyl group;
R⁴ represents hydrogen or $C_{1-4}$ alkyl group;

and/or geometric isomers and/or stereoisomers and/or diastereomers and/or salts and/or hydrates and/or solvates and/or polymorphs thereof.

In a further embodiment, the compound of formula (I) is selected from:
trans-N-(4-{2-[4-(5,6-dichloro-2-methylamino-pyrimidin-4-yl)-piperazin-1-yl]-ethyl]-cyclohexyl}-acetamide,
trans-(4-{2-[4-(5,6-dichloro-2-methylamino-pyrimidin-4-yl)-piperazin-1-yl]-ethyl}-cyclohexyl)-urea,
trans-morpholine-4-carboxylic acid (4-{2-[4-(5,6-dichloro-2-ethylamino-pyrimidin-4-yl)-piperazin-1-yl]-ethyl}-cyclohexyl)-amide,
trans-(4-{2-[4-(5,6-dichloro-2-ethylamino-pyrimidin-4-yl)-piperazin-1-yl]-ethyl}-cyclohexyl)-urea,
trans-N-(4-{2-[4-(5,6-dichloro-2-dimethylamino-pyrimidin-4-yl)-piperazin-1-yl]-ethyl}-cyclohexyl)-acetamide,
trans-N-(4-{2-[4-(5,6-dichloro-2-ethylamino-pyrimidin-4-yl)-piperazin-1-yl]-ethyl}-cyclohexyl)-acetamide,
trans-morpholine-4-carboxylic acid (4-{2-[4-(5,6-dichloro-2-methylamino-pyrimidin-4-yl)-piperazin-1-yl]-ethyl}-cyclohexyl)-amide,
trans-3-(4-{2-[4-(5,6-dichloro-2-methylamino-pyrimidin-4-yl)-piperazin-1-yl]-ethyl}-cyclohexyl-1,1-dimethyl-urea,
trans-3-(4-{2-[4-(5,6-dichloro-2-ethyl-amino-pyrimidin-4-yl)-piperazin-1-yl]-ethyl}-cyclohexyl}-1,1-dimethyl-urea,
trans-1-(4-{2-[4-(5,6-dichloro-2-methylamino-pyrimidin-4-yl)-piperazin-1-yl]-ethyl}-cyclohexyl)-3-ethyl-urea,
trans-N-(4-{2-[4-(5,6-dichloro-2-methylamino-pyrimidin-4-yl)-piperazin-1-yl]-ethyl}-cyclohexyl-propionamide,
trans-N-(4-{2-[4-(2-amino-5,6-dichloro-pyrimidin-4-yl)-piperazin-1-yl]-ethyl}-cyclohexyl)-acetamide,
trans-1-(4-{2-[4-(5,6-dichloro-2-methylamino-pyrimidin-4-yl)-piperazin-1-yl]-ethyl}cyclohexyl)-3-methyl-urea,
trans-N-(4-{2-[4-(5,6-dichloro-2-methylamino-pyrimidin-4-yl)-piperazin-1-yl]-ethyl}-cyclohexyl)-benzamide,
trans-3-bromo-N-(4-{2-[4-(5,6-dichloro-2-methylamino-pyrimidin-4-yl)-piperazin-1-yl]-ethyl}-cyclohexyl)-benzamide, and/or geometric isomers and/or stereoisomers and/or diastereomers and/or salts and/or hydrates and/or solvates and/or polymorphs thereof.

In another embodiment, the present invention includes compounds of formula (III):

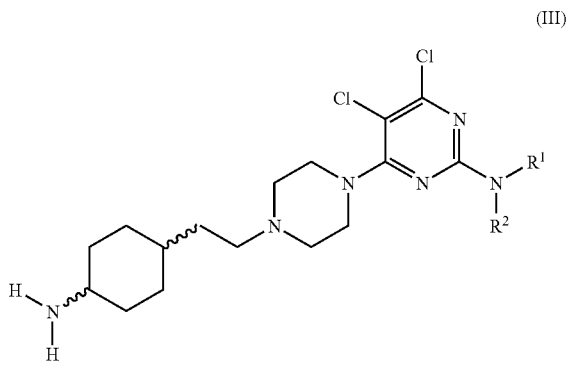

wherein
R$^1$ represents hydrogen or C$_{1-4}$ alkyl group, and
R$^2$ represents hydrogen or C$_{1-4}$ alkyl group.

In a further embodiment, the compound of formula (III) is selected from:
trans-(4-{4-[2-(4-amino-cyclohexyl)-ethyl]-piperazin-1-yl}-5,6-dichloro-pyrimidin-2-yl)-methyl-amine,
trans-(4-{4-[2-(4-amino-cyclohexyl)-ethyl]-piperazin-1-yl}-5,6-dichloro-pyrimidin-2-yl)-dimethyl-amine,
trans-(4-{4-[2-(4-amino-cyclohexyl)-ethyl]-piperazin-1-yl}-5,6-dichloro-pyrimidin-2-yl)-ethyl-amine,
trans-(4-{4-[2-(4-amino-cyclohexyl)-ethyl]-piperazin-1-yl}-5,6-dichloro-pyrimidin-2-yl)-amine.

Synthetic Processes

The present invention also provides processes for preparing compounds of formula (I).

In one embodiment, the present invention is directed to a process (Method A) for preparing compounds of formula (I) wherein Q represents C$_{1-4}$ alkyl, —NR$^3$R$^4$, phenyl, optionally substituted phenyl, 1-pyrrolidinyl, 1-piperidinyl, 4-R$^5$-piperazin-1-yl or 4-morpholinyl group, R$^1$ represents hydrogen or C$_{1-4}$ alkyl group, R$^2$ represents hydrogen or C$_{1-4}$ alkyl group, R$^3$ represents hydrogen, C$_{1-4}$ alkyl group, phenyl or optionally substituted phenyl, R$^4$ represents hydrogen, C$_{1-4}$ alkyl group, phenyl or optionally substituted phenyl, and R$^5$ represents hydrogen or C$_{1-4}$ alkyl group;

said process involving reacting an acid- or carbamoylchloride of formula (II):

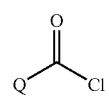

wherein Q is as described above;
with an amine of formula (III):

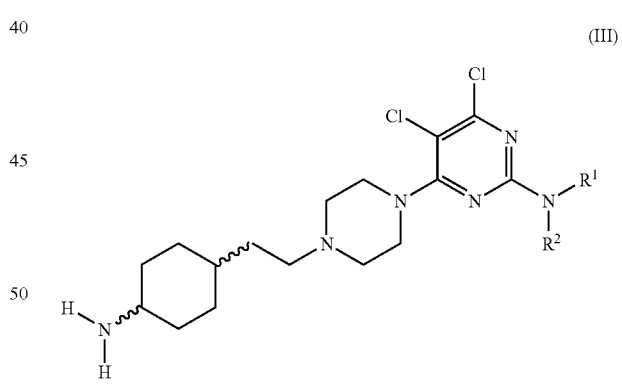

wherein
R$^1$ represents hydrogen or C$_{1-4}$ alkyl group, and
R$^2$ represents hydrogen or C$_{1-4}$ alkyl group.

The process of Method A may be carried out by methods known to one of ordinary skill in the art, for example, by suspending or dissolving the appropriate amine of formula (III), or a salt thereof, in a suitable solvent (e.g. tetrahydrofuran, dimethylformamide, chlorinated hydrocarbons or hydrocarbons) and adding the appropriate acid- or carbamoylchloride of formula (II) to this suspension or solution, in the presence of a base (e.g. triethylamine). The reaction can be carried out advantageously between about −10° C. and about 60° C. Reaction progress may be monitored by thin layer chromatography. The reaction time is typically about 6-60 h. Work-up of the reaction mixture can be carried out by different known methods. The products can be purified, e.g. by crystallization or by column chromatography.

In another embodiment, the present invention is directed to a process (Method B) for preparing compounds of formula (I) wherein Q represents $NR^3R^4$;
$R^1$ represents hydrogen or $C_{1-4}$ alkyl group;
$R^2$ represents hydrogen or $C_{1-4}$ alkyl group;
$R^3$ represents hydrogen, $C_{1-4}$ alkyl group, phenyl or optionally substituted phenyl; and
$R^4$ represents hydrogen, $C_{1-4}$ alkyl group, phenyl or optionally substituted phenyl, said process involving reacting an isocyanate of formula (IV):

$$R^6—NCO \quad (IV)$$

wherein $R^6$ represents $C_{1-4}$ alkyl group, phenyl or optionally substituted phenyl, with an amine of formula (III):

(III)

[Structure of compound III]

wherein
$R^1$ represents hydrogen or $C_{1-4}$ alkyl group,
$R^2$ represents hydrogen or $C_{1-4}$ alkyl group.

The process of Method B may be carried out by methods known to one of ordinary skill in the art, for example, by suspending or dissolving the appropriate amine of formula (III), or a salt thereof, in a suitable solvent (e.g. tetrahydrofuran, N,N-dimethylformamide, chlorinated hydrocarbons or hydrocarbons) and adding the appropriate isocyanate of formula (IV) to this suspension or solution, if necessary, in the presence of a base (e.g. triethylamine). The reaction can be carried out advantageously between about 5° C. and about 50° C. Reaction progress may be monitored by thin layer chromatography. The reaction time is typically about 6-10 h. Work-up of the reaction mixture can be carried out by different known methods. The products can be purified, e.g. by crystallization or by column chromatography.

In yet another embodiment, the present invention is directed to a process (Method C) for preparing compounds of formula (I) wherein Q represents amino
$R^1$ represents hydrogen or $C_{1-4}$ alkyl group,
$R^2$ represents hydrogen or $C_{1-4}$ alkyl group said process involving reacting a cyanate, e.g., potassium cyanate or sodium cyanate with an amine of formula (III)

(III)

[Structure of compound III]

wherein
$R^1$ represents hydrogen or $C_{1-4}$ alkyl group,
$R^2$ represents hydrogen or $C_{1-4}$ alkyl group.

The process reaction of Method C may be carried out by methods known to one of ordinary skill in the art, for example, the transformation a compound of formula (III) to a compound of formula (I) may be carried out in an alcoholic solvent (e.g. methyl or ethyl alcohol) in the presence of a base (e.g. triethylamine), and potassium or sodium cyanate advantageously at reflux temperature. The reaction time is typically about 2-24 hours. Work-up of the reaction mixture can be carried out by different known methods. The products can be purified, e.g. by crystallization or by column chromatography.

The acid- or carbamoylchlorides of formula (II) and the isocyanates of formula (IV) are either commercially available or can be synthesized by different methods known to one of ordinary skill in the art. Potassium and sodium cyanate salts are commercially available.

Compounds of formula (III) may be prepared by methods known to one of ordinary skill in the art, e.g. by reacting the aldehyde of formula (V):

(V)

[Structure of compound V]

wherein Boc is a tert-butoxycarbonyl group,
with a piperazine of formula (VI):

(VI)

[Structure of compound VI]

wherein the meaning of $R^1$ and $R^2$ is as described above for formula (III), under reductive amination conditions, followed by removal of the Boc protecting group. The reaction may be carried out in an inert solvent (e.g. chlorinated hydrocarbons, alkanols or ethers) in the presence of a reductive agent, for example, sodium borohydride, sodium cyanoborohydride or sodium triacetoxyborohydride. The reaction temperature is between about 0° C. and about room temperature. The reaction time is typically about 2-24 h. Deprotection may be carried out using, e.g., trifluoroacetic acid or hydrochloric acid in a suitable solvent.

Synthesis of aldehydes of formula (V) are described, e.g., in *J. Med. Chem.* 43, 1878, (2000).

Compounds of formula (VI) may synthesized by methods known to one of ordinary skill in the art, e.g. by reacting 1-Boc-piperazine with a pyrimidine of a formula (VII).

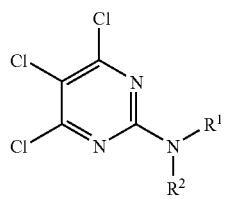

(VII)

wherein the meaning of $R^1$ and $R^2$ is as described above for formula (III), under alkylation conditions followed by removal of the Boc protecting group. The reaction may be carried out in an inert solvent (e.g. chlorinated hydrocarbons, hydrocarbons, acetonitrile, N,N-dimethylformamide and ketones) in the presence of organic or inorganic base (e.g. triethylamine, sodium or potassium carbonate) advantageously between about 60° C. and about 150° C. The reaction time is about typically 2-24 hours. Work-up of the reaction mixture can be carried out by different known methods. The products can be purified, e.g. by crystallization or by column chromatography. Deprotection may be carried out using, e.g., trifluoroacetic acid or hydrochloric acid.

Compounds of a formula (VII) are described, e.g., in *J. Med. Chem.*, 25, 1459, (1982). 1-Boc piperazine is commercially available.

Formulations

For use in medicine, the compounds of formula (I) of the present invention and/or geometric isomers and/or stereoisomers and/or diastereomers and/or physiologically acceptable salts and/or hydrates and/or solvates and/or polymorphs thereof are usually administered as a standard pharmaceutical composition. The present invention therefore provides in a further aspect pharmaceutical compositions comprising a compound of formula (I) and/or geometric isomers and/or stereoisomers and/or diastereomers and/or physiologically acceptable salts and/or hydrates and/or solvates and/or polymorphs thereof and physiologically acceptable carriers.

The compounds of formula (I) of the present invention and/or geometric isomers and/or stereoisomers and/or diastereomers and/or physiologically acceptable salts and/or hydrates and/or solvates and/or polymorphs thereof may be administered by any convenient method, for example by oral, parental, buccal, sublingual, nasal, rectal or transdermal administration and the pharmaceutical compositions adapted accordingly.

The compounds of formula (I) of the present invention and/or geometric isomers and/or stereoisomers and/or diastereomers and/or physiologically acceptable salts and/or hydrates and/or solvates and/or polymorphs thereof which are active when given orally can be formulated as liquids or solids, for example syrups, suspensions or emulsions, tablets, capsules and lozenges.

A liquid formulation of the compounds of formula (I) of the present invention and/or geometric isomers and/or stereoisomers and/or diastereomers and/or physiologically acceptable salts and/or hydrates and/or solvates and/or polymorphs thereof generally consists of a suspension or solution of the compound of formula (I) and/or geometric isomers and/or stereoisomers and/or diastereomers and/or salts and/or hydrates and/or solvates and/or polymorphs thereof in a suitable liquid carrier(s), for example an aqueous solvent, such as water, ethanol or glycerol, or a non-aqueous solvent, such as polyethylene glycol or an oil. The formulation may also contain one or more suspending agent, preservative, flavouring or colouring agent, or combinations thereof.

A composition in the solid form of a tablet can be prepared using any suitable pharmaceutical carrier(s) routinely used for preparing solid formulations. Examples of such carriers include magnesium stearate, starch, lactose, sucrose, cellulose, etc.

A composition in the solid form of a capsule can be prepared using routine encapsulation procedures. For example, pellets containing the active ingredient can be prepared using standard carriers and then filled into a hard gelatine capsule; alternatively, a dispersion or suspension can be prepared using any suitable pharmaceutical carrier(s), for example aqueous gums, celluloses, silicates or oils and the dispersion or suspension then filled into a soft gelatine capsule.

Parenteral compositions are typically a solution or suspension of the compound of formula (I) of the present invention and/or geometric isomers and/or stereoisomers and/or diastereomers and/or physiologically acceptable salts and/or hydrates and/or solvates and/or polymorphs thereof in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions of the present invention for nasal administration containing a compound of formula (I) and/or geometric isomers and/or stereoisomers and/or diastereomers and/or physiologically acceptable salts and/or hydrates and/or solvates and/or polymorphs thereof may conveniently be formulated as aerosols, drops, gels and powders. Aerosol formulations of the present invention typically comprise a solution or fine suspension of the compound of formula (I) and/or geometric isomers and/or stereoisomers and/or diastereomers and/or physiologically acceptable salts and/or hydrates and/or solvates and/or polymorphs thereof in a physiologically acceptable aqueous or non-aqueous solvent and are usually presented in a single or multidose quantities in sterile form is a sealed container, which can take the form of a cartridge or refill for use with an atomising device. Alternatively, the sealed container may be a unitary dispensing device, such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas, such as compressed air or an organic propellant, such as a fluorochlorohydrocarbon. The aerosol dosage form can also take the form of a pump-atomiser. Compositions of the present invention containing a compound of formula (I) and/or geometric isomers and/or stereoisomers and/or diastereomers and/or physiologically acceptable salts and/or hydrates and/or solvates and/or polymorphs thereof suitable for buccal or sublingual administration include tablets, lozenges and pastilles, wherein the active ingredient is formulated with a carrier, such as sugar and acacia, tragacanth, or gelatine and glycerol etc.

Compositions of the present invention containing a compound of formula (I) and/or geometric isomers and/or stereoisomers and/or diastereomers and/or physiologically acceptable salts and/or hydrates and/or solvates and/or polymorphs thereof for rectal administration are conveniently in the form of suppositories containing a conventional suppository base, such as cocoa butter.

Compositions of the present invention containing a compound of formula (I) and/or geometric isomers and/or stereoisomers and/or diastereomers and/or physiologically acceptable salts and/or hydrates and/or solvates and/or polymorphs thereof for transdermal administration include ointments, gels and patches.

The compositions of the present invention containing a compound of formula (I) and/or geometric isomers and/or stereoisomers and/or diastereomers and/or physiologically acceptable salts and/or hydrates and/or solvates and/or polymorphs thereof are preferably in a unit dose form, such as a tablet, capsule or ampoule.

The following are examples of suitable pharmaceutical formulations of the present invention.

a) Intravenous Injection

| Compound of formula (I) | 1-40 mg |
| --- | --- |
| Buffer | to pH ca 7 |
| Solvent/complexing agent | to 100 ml | b) Bolus Injection

| Compound of formula (I) | 1-40 mg |
| --- | --- |
| Buffer | to pH ca 7 |
| Co-solvent | to 5 ml |

Buffer: suitable buffers include citrate, phosphate, sodium hydroxide/hydrochloric acid.
Solvent: typically water but may also include cyclodextrins (1-100 mg) and co-solvents, such as propylene glycol, polyethylene glycol and alcohol.

c) Tablet

| Compound of formula (I) | 1-40 mg |
| --- | --- |
| Diluent/Filter(may also include cyclodextrins) | 50-250 mg |
| Binder | 5-25 mg |
| Disintegrant (may also include cyclodextrins) | 5-50 mg |
| Lubricant | 1-5 mg |
| Cyclodextrin | 1-100 mg |

Diluent: e.g. microcrystalline cellulose, lactose starch.
Binder: e.g. polyvinylpyrrolidone, hydroxypropylmethylcellulose.
Disintegrant: e.g. sodium starch glycolate, crospovidone.
Lubricant: e.g. magnesium stearate, sodium stearyl fumarate d) Oral Suspension

| Compound of formula (I) | 1-40 mg |
| --- | --- |
| Suspending agent | 0.1-10 mg |
| Diluent | 20-60 mg |
| Preservative | 0.01-1.0 mg |
| Buffer | to pH ca 5-8 |
| Co-solvent | 0-40 mg |
| Flavour | 0.01-1.0 mg |
| Colourant | 0.001-0.1 mg |

Suspending agent: e.g. xanthan gum, microcrystalline cellulose.
Diluent: e.g. sorbitol solution, typically water.
Preservative: e.g. sodium benzoate.
Buffer: e.g. citrate.
Co-solvent: e.g. alcohol, propylene glycol, polyethylene glycol, cyclodextrin.

Methods of Treatment

The compounds of formula (I) of the present invention, in contrast to known antipsychotics, have been found to exhibit very high affinity for dopamine $D_3$ receptors, high-to-moderate affinity for dopamine $D_2$ receptors and no affinity for adrenergic alpha-1 receptors. The compounds are expected to be useful in the treatment and/or prevention of disease states in which $D_3$ and/or $D_2$ receptors are involved in the disease pathology and thus their modulation is required, or in which modulation of $D_3$ and/or $D_2$ receptors exerts beneficial effect on the state and/or process of the disease.

Dysfunction of the dopaminergic neurotransmitter system is involved in the pathology of several neuropsychiatric and neurodegenerative disorders such as schizophrenia, mania, bipolar disorders, drug abuse, dementia, cognitive dysfunctions, and Parkinson's disease. The effects of neurotransmitter dopamine is mediated via at least five distinct dopamine receptors belonging to D1- (i.e. $D_1$ and $D_5$) or $D_2$- (i.e. $D_2$, $D_3$ and $D_4$) families. $D_3$ receptors have been shown to have characteristic distribution in the mammalian brain. Namely, they were found in high densities in certain limbic structures such as nucleus accumbens, olfactory tubercle and islands of Calleja. Therefore, preferential targeting of the $D_3$ receptors may be a promising approach for more selective modulation of certain dopaminergic functions and consequently offers successful therapeutic interventions in several abnormalities such as schizophrenia, emotional or cognitive dysfunctions (see, e.g., Sokoloff, P. et al.: Nature 1990, 347:146; Schwartz, J. C. et al.: Clin. Neuropharmacol. 1993, 16:295; Schwartz, J. C. et al.: Brain Res. Rev. 2000, 31:277; Levant, B.: Pharmacol, Rev. 1997, 49:231; Laszy, J. et al.: Psychopharmacol. 2005, 179:567), drug abuse (see, e.g., Pilla, C. et al.: Nature 199, 400:371; Heidbreder, C. A. et al.: Brain Res. Rev. 2005, 49:77), Parkinson's disease (see, e.g., Levant, B. et al.: CNS Drugs 1999, 12:391; Joyce, J. N.: Pharmacol. Therap. 2001, 90:231; Bézard, E. et al.: Nature Medicine 2003, 9:762) and pain (see, e.g., Levant, B. et al.: Neurosci. Lett. 2001, 303:9).

The dopamine $D_2$ receptors are widely distributed in the brain and are known to be involved in numerous physiological functions and pathological states. $D_2$ antagonists are, for example, widely used as antipsychotics. However, it is also well known that massive antagonism of the $D_2$ receptors leads to unwanted side effects, such as extrapyramidal motor symptoms, psychomotor sedation, cognitive blunting and endocrine alterations. These side effects seriously restrict the therapeutic utilization of $D_2$ antagonist compounds (see, e.g., Wong, A. H. C. et al.: Neurosci. Biobehav. Rev. 2003, 27:269; Stahl, S. M. 2002, Essential Psychopharmacology. Neuroscientific Basis and Practical Applications. $2^{nd}$ Ed. Cambridge University Press).

Cardiovascular side effects (such as orthostatic hypotension associated with dizziness, tachycardia and sometimes syncope) of the first generation antipsychotics (e.g. chlorpromazine, thioridazine, chlorprothixene) and second generation antipsychotics (e.g. olanzapine, risperidone) are well documented (see, e.g., Pacher, P. and Kecskeméti, V.: Curr. Pharm. Des. 2004, 10:2463; Brunton, L., Lazo, J. and Parker, K. (eds) Goodman and Gilman's The Pharmacological Basis of Therapeutics, 11th Edition, Mc Graw Hill, 2005, p. 462; Stahl, S. M. 2002, Essential Psychopharmacology. Neuroscientific Basis and Practical Applications. $2^{nd}$ Ed. p. 409, Cambridge University Press, 2000; http://www.fda.gov/medwatch/safety/2006/Sep_Pls/RisperdalConsta_Pl.pdf; http://www.fda.gov/medwatch/safety/2006/Aug_Pls/Zyprexa_Pl.pdf). Side effects of this sort hamper or seriously limit the antipsychotic therapy especially in the initial period. All the above mentioned first and second generation antipsychotics show considerable (i.e. nanomolar) affinities to adrenergic alpha-1 receptors and it is a common view that the majority of their cardiovascular side effects are mainly related to their alpha-1 antagonist actions. Thus, the lack of adrenergic alpha-1 activity is a highly desirable feature of a potential antipsychotic compound.

The present invention provides novel compounds of formula (I) and/or geometric isomers and/or stereoisomers and/or diastereomers and/or salts and/or hydrates and/or solvates and/or polymorphs thereof which have high affinity for dopamine $D_3$ receptors (Ki values less than 3 nM) and, simultaneously, have high-to-moderate affinity for dopamine $D_2$ receptors (Ki values of 10 to 50 nM) always in a such combination that the $D_3$ affinity is 5 to 50-times higher than the $D_2$ affinity. In addition, compounds of formula (I) have no affinity to adrenergic alpha-1 receptors.

In a further aspect, the present invention provides a method of treating conditions which require preferential modulation of dopamine $D_3$ and/or $D_2$ receptors, such as, but not limited to, psychoses (e.g. schizophrenia, schizo-affective disorders), cognitive impairment accompanying schizophrenia, mild-to-moderate cognitive deficits, dementia, psychotic states associated with dementia, psychotic depression, mania, bipolar disorder, paranoid and delusional disorders, dyskinetic disorders such as Parkinson's disease, neuroleptic induced parkinsonism, tardive dyskinesia, eating disorders (e.g. bulimia nervosa), attention deficit disorders, hyperactivity disorders, depression and depressive states, anxiety disorders, sexual dysfunctions (e.g. erectile dysfunctions), sleep disorders, emesis, aggression, autism, drug (e.g. alcohol, cocaine, nicotine, opioids) abuse and pain, which comprises administering to a subject in need thereof an effective amount of a compound of formula (I) and/or geometric isomers and/or stereoisomers and/or diastereomers and/or salts and/or hydrates and/or solvates and/or polymorphs thereof.

The invention also provides the use of a compound of formula (I) and/or geometric isomers and/or stereoisomers and/or diastereomers and/or salts and/or hydrates and/or solvates and/or polymorphs thereof in the manufacture of a medicament for the treatment of conditions which require modulation of dopamine receptors, especially dopamine $D_3$ and/or $D_2$ receptors.

A preferred use for $D_3/D_2$ ligands according to the present invention is in the treatment of schizophrenia, schizo-affective disorders, cognitive impairment accompanying schizophrenia, mild-to-moderate cognitive deficits, dementia, psychotic states associated with dementia, psychotic depression, mania, bipolar disorder, paranoid and delusional disorders, dyskinetic disorders such as Parkinson's disease, neuroleptic induced parkinsonism, depression and depressive states, anxiety disorders, and drug abuse (e.g. cocaine abuse).

The particular combination of the two receptor-actions described above allows the simultaneous manifestation of the beneficial actions of $D_3$ functional antagonism (e.g. cognitive enhancer effect, inhibition of extrapyramidal motor symptoms, inhibitory action on drug abuse) and that of the $D_2$ functional antagonism (e.g. antipsychotic effect). Furthermore, the same combination surprisingly results in cancelling out the disadvantageous features of $D_2$ antagonism (e.g. extrapyramidal symptoms, psychomotor sedation, cognitive disturbances).

EXAMPLES

The present invention will now be further described by way of the following non-limiting examples. In applying the disclosure of these examples, it should be kept clearly in mind that the examples are merely illustrative of the present invention and should not be construed as limiting the scope of the invention in any way as many variations and equivalents that are encompassed by the present invention will become apparent to those skilled in the art upon reading the present disclosure.

The structure of all intermediates and end products were elucidated by IR, NMR and MS spectroscopy.

Example 1

4-(5,6-dichloro-2-methylamino-pyrimidin-4-yl)-piperazine-1-carboxylic acid tert-butyl ester (Intermediate Compound 1a)

Methyl-(4,5,6-trichloro-pyrimidin-2-yl)-amine (2.8 g, 12.2 mmol), 1-Boc-piperazine (2.27 g, 12.2 mmol), potassium carbonate (0.84 g 6.1 mmol) in water (2.5 ml) and methyl ethyl ketone (50 ml) were refluxed for 12 hours. After cooling to room temperature the precipitate was filtered, and washed with water to give the title compound (2.6 g, 59%), melting point: 205-206° C.

Applying the above procedure the following compounds were prepared:

4-(5,6-dichloro-2-dimethylamino-pyrimidin-4-yl)-piperazine-1-carboxylic acid tert-butyl ester, melting point: 129-131° C. (intermediate compound 1b);

4-(5,6-dichloro-2-ethylamino-pyrimidin-4-yl)-piperazine-1-carboxylic acid tert-butyl ester, melting point: 164-167° C. (intermediate compound 1c);

4-(2-amino-5,6-dichloro-pyrimidin-4-yl)-piperazine-1-carboxylic acid tert-butyl ester, melting point: 170-175° C. (intermediate compound 1d).

Example 2

(4,5-Dichloro-6-piperazin-1-yl-pyrimidin-2-yl)-methyl-amine dihydrochloride (Intermediate Compound 2a)

2.6 g (7.2 mmol) 4-(5,6-dichloro-2-methylamino-pyrimidin-4-yl)-piperazine-1-carboxylic acid tert-butyl ester was deprotected at 10° C. using 100 ml ethylacetate saturated with gaseous hydrochloric acid. After 4 hours the precipitate was filtered giving the title compound (2.4 g, 100%), melting at 204-209° C.

Applying the above procedure the following compounds were prepared:

(4,5-dichloro-6-piperazin-1-yl-pyrimidin-2-yl)-dimethyl-amine dihydrochloride, melting point: 178-184° C. (intermediate compound 2b);

(4,5-dichloro-6-piperazin-1-yl-pyrimidin-2-yl)-ethyl-amine dihydrochloride, melting point: 200-202° C. (intermediate compound 2c);

(4,5-dichloro-6-piperazin-1-yl-pyrimidin-2-yl)-amine dihydrochloride, melting point: 183-185° C. (intermediate compound 2d).

Example 3

Trans-(4-{2-[4-(5,6-dichloro-2-methylamino-pyrimidin-4-yl)-piperazin-1-yl]-ethyl}-cyclohexyl)-carbamic acid tert-butyl ester (Intermediate Compound 3a)

5.36 g (16 mmol) of (4,5-dichloro-6-piperazin-1-yl-pyrimidin-2-yl)-methyl-amine dihydrochloride and 3.86 g (16 mmol) of trans-4-(2-oxoethyl)cyclohexyl-carbamic acid tert-butyl ester were dissolved in dichloromethane (320 ml). 6.7 ml (48 mmol) triethylamine was added, then 5.1 g (24 mmol) sodium triacetoxyborohydride was added portion wise and the reaction mixture was stirred for 20 hours at ambient temperature. 20% potassium carbonate solution in water (100 ml) was then added. The organic layer was separated, dried and evaporated to dryness in vacuo. The residue was triturated with diethyl ether to give the title compound (6.9 g, 88.5%), melting point: 199-202° C.

Applying the above procedure the following compounds were prepared:

trans-(4-{2-[4-(5,6-dichloro-2-dimethylamino-pyrimidin-4-yl)-piperazin-1-yl]-ethyl}-cyclohexyl)-carbamic acid tert-butyl ester melting point: 169-171° C. (intermediate compound 3b);

trans-(4-{2-[4-(5,6-dichloro-2-ethylamino-pyrimidin-4-yl)-piperazin-1-yl]-ethyl}-cyclohexyl)-carbamic acid tert-butyl ester melting point: 164-168° C. (intermediate compound 3c);

trans-(4-{2-[4-(2-amino-5,6-dichloro-pyrimidin-4-yl)-piperazin-1-yl]-ethyl}-cyclohexyl)-carbamic acid tert-butyl ester, melting point: 197-199° C. (intermediate compound 3d).

Example 4

Trans-(4-{4-[2-(4-amino-cyclohexyl)-ethyl]-piperazin-1-yl}-5,6-dichloro-pyrimidin-2-yl)-methyl-amine trihydrochloride (Intermediate Compound 4a)

4.88 g (10 mmol) trans-(4-{2-[4-(5,6-dichloro-2-methylamino-pyrimidin-4-yl)-piperazin-1-yl]-ethyl}-cyclohexyl)-carbamic acid tert-butyl ester was deprotected at 10° C. using 100 ml ethylacetate saturated with gaseous hydrochloric acid. After 4 hours the precipitate was filtered giving the title compound (4.9 g, 99%), melting at 325-326° C.

Applying the above procedure the following compounds were prepared:

trans-(4-{4-[2-(4-amino-cyclohexyl)-ethyl]-piperazin-1-yl}-5,6-dichloro-pyrimidin-2-yl)-dimethyl-amine trihydrochloride, melting point: 329-330° C. (intermediate compound 4b)

trans-(4-{4-[2-(4-amino-cyclohexyl)-ethyl]-piperazin-1-yl}-5,6-dichloro-pyrimidin-2-yl)-ethyl-amine trihydrochloride, melting point: 318-319° C. (intermediate compound 4c)

trans-(4-{4-[2-(4-amino-cyclohexyl)-ethyl]-piperazin-1-yl}-5,6-dichloro-pyrimidin-2-yl)-amine trihydrochloride, melting point: 324-326° C. (intermediate compound 4d)

Method A

Trans-N-(4-{2-[4-(5,6-dichloro-2-methylamino-pyrimidin-4-yl)-piperazin-1-yl]-ethyl}-cyclohexyl)-acetamide (Compound 1)

2.28 g (4.6 mmol) trans-(4-{4-[2-(4-amino-cyclohexyl)-ethyl]-piperazin-1-yl}-5,6-dichloro-pyrimidin-2-yl)-methyl-amine trihydrochloride was suspended in dichloromethane (50 ml). Triethylamine (3.5 ml, 25.3 mmol) was added followed by the addition of acetyl chloride (0.49 ml, 6.9 mmol). The reaction mixture was stirred for 24 hours at room temperature. The precipitate was filtered, washed with water and purified using column chromatography to give the title compound (1.39 g, 70%), MS (EI): 430.2 (MH$^+$); $^1$H NMR (300 MHz, DMSO-d$_6$ (TMS)+1 drop of cc. DCl, □ (ppm)): 0.89-0.96 m (2H); 1.06-1.35 m (3H); 1.55-1.82 m (6H); 1.79 s (3H); 2.76 (3H); 2.98-3.18 m (4H); 3.37-3.58 m (5H); 4.16-4.29 m (2H); 7.90 br (residual NH); 11.35 br (residual NH).

Method B

Trans-1-(4-{2-[4-(5,6-dichloro-2-methylamino-pyrimidin-4-yl)-piperazin-1-yl]-ethyl}-cyclohexyl)-3-ethyl-urea (Compound 10)

0.25 g (0.5 mmol) trans-(4-{4-[2-(4-amino-cyclohexyl)-ethyl]-piperazin-1-yl}-5,6-dichloro-pyrimidin-2-yl)-methyl-amine trihydrochloride was dissolved in dry dichloromethane (10 ml). Triethylamine (0.28 ml, 2 mmol) was added followed by the addition of ethylisocyanate (0.06 ml, 0.753 mmol), and the reaction mixture was stirred at room temperature for 4 hours. The solvent was removed in vacuo. The residue was triturated with water, and the precipitate was filtered to give the title compound (0.17 g, 72%) MS (EI): 459.2 (MH$^+$). $^1$H NMR (300 MHz, DMSO-d$_6$ (TMS)+1 drop of cc. DCl, □ (ppm)): 0.96 t (3H); 0.88-1.13 m (4H); 1.13-1.31 m (1H); 1.54-1.85 m (6H); 2.74 s (3H); 2.98 q (2H); 2.89-3.16 m (4H); 3.19-3.33 m (1H); 3.34-3.58 m (4H); 4.12-4.30 m (2H).

Method C

Trans-(4-{2-[4-(5,6-dichloro-2-methylamino-pyrimidin-4-yl)-piperazin-1-yl]-ethyl}-cyclohexyl)-urea (Compound 2)

0.6 g (1.3 mmol) trans-(4-{4-[2-(4-amino-cyclohexyl)-ethyl]-piperazin-1-yl}-5,6-dichloro-pyrimidin-2-yl)-methyl-amine trihydrochlorid was suspended in methanol. Triethylamine (0.36 ml, 2.6 mmol) was added followed by the addition potassium cyanate (0.26 g, 3.12 mmol). The mixture was refluxed for 10 hours. The solvent was removed in vacuo. The residue was triturated with water, and the precipitate was filtered to give the title compound (0.42 g 75%) MS (EI): 431.2 (MH$^+$). $^1$H NMR (300 MHz, DMSO-d$_6$ (TMS)+1 drop of cc. DCl, □ (ppm)): 0.91-1.12 m (2H); 1.15-1.36 m (3H); 1.56-1.92 m (6H); 2.76 s (3H); 3.00-3.21 m (4H); 3.30-3.61 m (5H); 4.15-4.31 m (2H).

Applying one of the above methods, using the appropriate reactants, the following compounds were prepared:

trans-morpholine-4-carboxylic acid (4-{2-[4-(5,6-dichloro-2-ethylamino-pyrimidin-4-yl)-piperazin-1-yl]-ethyl}-cyclohexyl)-amide (Compound 3), MS (EI): 515.2 (MH$^+$); $^1$H NMR (300 MHz, DMSO-d$_6$ (TMS), □ (ppm)): 0.84-1.03 m (2H); 1.08 t (3H); 1.12-1.27 m (3H); 1.27-1.40 m (2H); 1.66-1.83 m (4H); 2.24-2.51 m (6H); 3.16-3.27 m (6H); 3.35-3.42 m (1H); 3.43-3.59 m (8H); 6.14 d (1H); 7.40 br. (1H);

trans-(4-{2-[4-(5,6-dichloro-2-ethylamino-pyrimidin-4-yl)-piperazin-1-yl]-ethyl}-cyclohexyl)-urea (Compound 4), MS (EI): 445.2 (MH$^+$); $^1$H NMR (300 MHz, DMSO-d$_6$ (TMS)+1 drop of cc. TFA, □ (ppm)): 0.86-1.18 m (4H); 1.10 s (3H); 1.15-1.32 m (1H); 1.49-1.61 m (2H); 1.65-1.89 m (4H); 3.03-3.37 m (9H); 3.49-3.62 m (2H); 4.18-4.36 m (2H);

trans-N-(4-{2-[4-(5,6-dichloro-2-dimethylamino-pyrimidin-4-yl)-piperazin-1-yl]-ethyl}-cyclohexyl)-acetamide (Compound 5), MS (EI): 444.3 (MH$^+$); $^1$H NMR (300 MHz, DMSO-d$_6$+1drop of cc. TFA (TMS), □ (ppm)): 0.91-1.34 m (5H); 1.45-1.62 m (2H); 1.66-1.85 m (4H); 1.77 s (3H); 3.07 s (6H); 3.07-3.20 m (4H); 3.20-3.36 m (2H); 3.37-3.62 m (3H); 4.22-4.36 m (2H); 7.71 d (1H); 9.77 br (due to protonation);

trans-N-(4-{2-[4-(5,6-dichloro-2-ethylamino-pyrimidin-4-yl)-piperazin-1-yl]-ethyl}-cyclohexyl)-acetamide (Compound 6), MS (EI): 444.2 (MH$^+$); $^1$H NMR (300 MHz, CDCl$_3$ (TMS), □ (ppm)): 1.04-1.14 m (4H); 1.19 t (3H); 1.23-1.30 m (1H); 1.37-1.48 m (2H); 1.77-1.82 m (2H); 1.95 s (3H); 1.94-2.04 m (2H); 2.34-2.43 m (2H); 2.48-2.55 m (4H); 3.30-3.43 m (2H); 3.58-3.77 m (5H); 4.83 t (1H); 5.23 d (1H);

trans-morpholine-4-carboxylic acid (4-{2-[4-(5,6-dichloro-2-methylamino-pyrimidin-4-yl)-piperazin-1-yl]-ethyl}-cyclohexyl)-amide (Compound 7), MS (EI): 501.2 (MH$^+$); $^1$H NMR (500 MHz, DMSO-d$_6$+DCl (TMS), □ (ppm)): 0.91-1.04 m (2H); 1.12-1.30 m (3H); 1.55-1.66 m (2H); 1.67-1.84 m (4H); 2.76 s (3H); 3.01-3.15 m (4H); 3.19-3.28 m (4H); 3.34-3.43 m (1H); 3.42-3.63 m (8H); 4.03-4.37 m (2H); 7.45 br (residual NH); 11.22 br (residual NH);

trans-3-(4-{2-[4-(5,6-dichloro-2-methylamino-pyrimidin-4-yl)-piperazin-1-yl]-ethyl}-cyclohexyl-1,1-dimethyl-urea (Compound 8), MS (EI): 459.2 (MH$^+$); $^1$H NMR (500 MHz, DMSO-d$_6$ (TMS)+1 drop of cc. TFA, □ (ppm)): 0.91-1.06 m (2H); 1.14-1.31 m (3H); 1.49-1.64 m (2H); 1.67-1.84 m (4H); 2.77 s (9H); 3.03-3.21 m (4H); 3.21-3.43 m (3H); 3.51-3.62 m (2H); 4.14-4.44 m (2H); 5.49 br. (due to protonation); 7.50 br (1H); 9.83 br (1H);

trans-3-(4-{2-[4-(5,6-dichloro-2-ethylamino-pyrimidin-4-yl)-piperazin-1-yl]-ethyl}-cyclohexyl}-1,1-dimethyl-urea (Compound 9), MS (EI): 473.2 (MH$^+$); $^1$H NMR (500 MHz, DMSO-d$_6$ (TMS)+1 drop of cc. TFA, □ (ppm)): 0.91-1.03 m (2H); 1.09 t (3H); 1.13-1.28 m (3H); 1.50-1.60 m (2H); 1.66-1.84 m (4H); 2.75 s (6H); 3.00-3.19 m (4H); 3.19-3.39 m (5H); 3.48-3.62 m (2H); 4.07-4.36 m (2H); 5.86 br (due to protonation); 7.53 br (1H); 9.91 br (1H);

trans-N-(4-{2-[4-(5,6-dichloro-2-methylamino-pyrimidin-4-yl)-piperazin-1-yl]-ethyl}-cyclohexyl-propionamide (Compound 11), MS (EI): 444.2 (MH$^+$) $^1$H NMR (500 MHz, DMSO-d$_6$ (TMS) 1 drop of cc. TFA, □ (ppm)): 0.97 t (3H); 0.95-1.05 m (2H); 1.06-1.18 m (2H); 1.18-1.29 m (1H); 1.51-1.59 m (2H); 1.68-1.81 m (4H); 2.03 q (2H); 2.76 s (3H); 3.03-3.34 m (6H); 3.40-3.51 m (1H); 3.51-3.60 m (2H); 4.13-4.39 m (2H); 7.42, 7.52 br. (due to protonation); 7.60 d (1H); 9.72 br. (1H);

trans-N-(4-{2-[4-(2-amino-5,6-dichloro-pyrimidin-4-yl)-piperazin-1-yl]-ethyl}-cyclohexyl)-acetamide (Compound 12), MS (EI): 416.2 (MH$^+$); $^1$H NMR (300 MHz, DMSO-d$_6$ (TMS), □ (ppm)): 0.83-1.28 m (5H); 1.28-1.40 m (2H); 1.65-1.82 m (4H); 1.76 s (3H); 2.26-2.35 m (2H); 2.37-2.48 m (4H); 3.35-3.54 m (5H); 7.65 d (1H); 6.83 s (2H);

trans-1-(4-{2-[4-(5,6-dichloro-2-methylamino-pyrimidin-4-yl)-piperazin-1-yl]-ethyl}-cyclohexyl)-3-methyl-urea (Compound 13), MS (EI): 445.3 (MH$^+$); $^1$H NMR (400 MHz, DMSO-d$_6$ (TMS)+1 drop of cc. DCl, □ (ppm)): 0.90-1.17 m (4H); 1.19-1.31 m (1H); 1.58-1.84 m (6H); 2.54 s (3H); 2.76 s (3H); 3.02-3.16 m (4H); 3.22-3.33 m (1H); 3.42-3.57 m (4H); 4.10-4.30 m (2H); 7.44 br (residual NH); 11.33 br (residual NH)

trans-N-(4-{2-[4-(5,6-dichloro-2-methylamino-pyrimidin-4-yl)-piperazin-1-yl]-ethyl}-cyclohexyl)-benzamide (Compound 14), MS (EI): 492.4 (MH$^+$); $^1$H NMR (400 MHz, DMSO-d$_6$ (TMS)+1 drop of cc. DCl, □ (ppm)): 0.98-1.11 m (2H); 1.21-1.44 m (3H); 1.61-1.70 m (2H); 1.73-1.90 m (4H); 2.76 s (3H); 2.97-3.19 m (4H); 3.42-3.56 m (4H); 3.66-3.83 m (1H); 4.09-4.32 m (2H); 7.41-7.54 m (3H); 7.82-7.87 m (2H); 8.26 br (residual NH); 11.33 br (residual NH);

trans-3-bromo-N-(4-{2-[4-(5,6-dichloro-2-methylamino-pyrimidin-4-yl)-piperazin-1-yl]-ethyl}-cyclohexyl)-benzamide (Compound 15), MS (EI): 571.3 (MH$^+$); $^1$H NMR (400 MHz, CDCl$_3$+MeOD-d$_4$ (TMS), □ (ppm)): 1.06-1.42 m (5H); 1.48-1.65 m (2H); 1.79-1.88 m (2H); 2.04-2.13 m (2H); 2.43-2.85 m (6H); 2.91 s (3H); 3.62-3.99 m (5H); 7.29-7.32 m (1H); 7.59-7.64 m (1H); 7.66-7.71 m (1H); 7.87-7.90 m (1H).

Biological Test Methods

1. D$_3$ Receptor Binding

Binding assays were carried out on rat recombinant D$_3$ receptors (Perkin-Elmer, Cat. No. 6110139) expressed in Sf9 cells using [$^3$H]spiperone (0.44-1.49 nM) as ligand and haloperidol (10 µM) for determination of non-specific binding. The assay was performed according to the supplier's assay protocol (Cat. No.: 3110139).

2. D$_2$ Receptor Binding

D$_2$ receptor binding was determined as described by Creese et al. (*Eur. J. Pharmacol.*, 60:55-66, 1979) on rat brain striatal membrane preparation using [$^3$H]spiperone (0.4-1.3 nM) as ligand. Non-specific binding was determined in the presence of 1 µM (+) butaclamol.

3. Alpha-1 Receptor Binding

Alpha-1 receptor binding studies were performed according to the methods described by Greengrass and Bremner (*Eur. J. Pharmacol.*, 55:323-326, 1979) on rat cortical membrane preparation using [$^3$H]-prazosine (0.22-0.37 nM) as ligand. The non-specific binding was determined in the presence of 10 µM phentolamine.

4. Amphetamine-Induced Hypermotility

One hour after the oral administration of doses of the test compound or vehicle, male Wistar rats were subcutaneously treated with d-amphetamine (0.5 mg/kg, sc.) and were individually placed in activity cages for one hour. Locomotor activity was measured in a four-channel activity monitor equipped with infrared photobeams Horizontal movement was determined as the number of beam interruptions. Mean±SE of horizontal activity data of each group was calculated. Percent inhibition of amphetamine-induced increase in locomotion was calculated for each dose of the tested compound. The ED-50 value was determined by linear regression fitted to the dose-response plot.

5. Catalepsy Test

Thirty minutes after the oral treatment with the test compounds male Wistar rats weighing 200-220 g (n=10/group) were placed in extra-ordinary position: placing both forepaws of the rat on a 10 cm high podium. Animals were considered to be cataleptic if they did not correct their body posture within 30 sec. The frequency of cataleptic animals was determined at one, two, three, four and five hours after the treatment. Minimum effective (cataleptic) dose was defined as the dose causing catalepsy at least at two readings (i.e. either at two time points in the same animal or in two different animals at any of the time points).

6. Scopolamine-Induced Learning Disturbance in the Water-Labyrinth

The learning process of rats was assessed in a 3-choice point water-labyrinth system. The number of directional turning errors was recorded in three daily trials for three experimental days. Male Wistar rats weighing 180-200 g (n=10 per groups) were treated orally with vehicle or the test compounds 1 hour before each daily session. Scopolamine (3 mg/kg ip.) as amnestic agent was injected 30 minutes prior to the first daily trial. Mean±SE of errors committed in all the trials was calculated in each group. Percent inhibition of scopolamine-induced increase in the number of errors was calculated for each dose of the tested compound.

Dopamine D$_3$ and D$_2$ and adrenergic alpha-1 receptor binding data of selected compounds of the present invention are listed in Table 1. Ki (nM) data are given.

TABLE 1

| Compound | $D_3$ Ki (nM) | $D_2$ Ki (nM) | Sel. | α-1 Ki (nM) | Sel. |
|---|---|---|---|---|---|
| 1 | <1 | 15-50 | 22 | >>1000 | n.a. |
| 2 | 1-3 | 15-50 | 27 | >>1000 | n.a. |
| 6 | 1-3 | 15-50 | 23 | >>1000 | n.a. |
| 7 | 1-3 | 5-15 | 7 | >>1000 | n.a. |
| 8 | 1-3 | 15-50 | 7 | >>1000 | n.a. |
| 10 | <1 | 5-15 | 17 | >>1000 | n.a. |
| 11 | <1 | 5-15 | 43 | >>1000 | n.a. |
| Olanzapine | 76 | 96 | 1.3 | 25.1 | 0.33 |
| Risperidone | 13 | 13 | 1.0 | 0.88 | 0.07 | n.a.: not applicable, due to the lack of alpha-1 binding
Sel. = $D_2/D_3$ selectivity, i.e., Ki for $D_2$ receptor divided by Ki for $D_3$ receptor The most prominent side effects of the first generation antipsychotic compounds (e.g. chlorpromazine and haloperidol) and at higher doses even those of second generation (atypical) antipsychotics (e.g. risperidone) are the extrapyramidal symptoms such as pseudo-parkinsonism and tardive dyskinesia and the orthostatic hypotension. The former two are the result of massive blockade of $D_2$ receptors in the basal ganglia whereas the latter is the consequence of antagonism of alpha-1 receptors.

As can be seen from Table 1, the compounds of the present invention are very highly potent ligands at $D_3$ receptors (Ki values are less than 3 nM) and moderately potent ligands at dopamine $D_2$ receptors (Ki values between 5 and 50 nM) showing 5 to 50 fold selectivity for $D_3$ over $D_2$ receptors. Coupling the very high $D_3$ affinity to the moderate $D_2$ affinity in this particular proportion allows the beneficial (e.g. antipsychotic) actions of a $D_2$ antagonist to be preserved, while at the same time, impeding (by the $D_3$ effects) the appearance of the disadvantageous consequences of massive $D_2$ receptor blockade, such as extrapyramidal symptoms or cognitive disturbances. It is therefore anticipated that no or greatly diminished adverse effects related to $D_2$ receptors will occur in the course of therapeutical application of compounds of the present invention. Furthermore, as well as favourably modulating the dopamine $D_2$ receptor-mediated functions, action of the compounds of formula (I) of the present invention on dopamine $D_3$ receptors will also result in additional therapeutically beneficial effects e.g. cognitive improvement, diminution of negative and depressive symptoms. In addition, the compounds have no affinity to adrenergic alpha-1 receptors (Ki values are higher than 1000 nM for each compound) and thus have extremely high $D_3$/alpha-1 selectivity. From the lack of affinity of the compounds to adrenergic alpha-1 receptors the lack of cardiovascular side effects (e.g. orthostatic hypotension and associated symptoms such as dizziness, tachycardia) is anticipated.

The beneficial effects of the compounds of formula (I) of the present invention carrying the above described particular combination of $D_3$ and $D_2$ receptor binding affinities were demonstrated in vivo, in methods used to measure antipsychotic effect (amphetamine hypermotility), cognitive enhancer activity (scopolamine-induced learning disturbance) and extrapyramidal side-effect (catalepsy test). The results are shown in Tables 2 and 3.

TABLE 2

Effects of compounds of formula (I) on amphetamine-induced hypermotility and in the catalepsy test

| compound | Inhibition of amphetamine-induced hypermotility (ED50, mg/kg) | Catalepsy (MED, mg/kg) | TI[a] |
|---|---|---|---|
| 1 | 0.14 | 100 | 714 |
| 8 | 0.14 | >25 | >179 |
| Olanzapine | 1.8 | 40 | 22 |
| Risperidone | 0.15 | 6.0 | 40 |

[a] therapeutic index - catalepsy MED divided by amphetamine hypermotility ED50

As can be seen from Table 2, compounds of formula (I) of the present invention have highly potent antipsychotic activity (inhibition of amphetamine-induced hypermotility) as can be predicted from their high to moderate dopamine $D_2$ receptor affinities. With regard to cataleptogenic (i.e. extrapyramidal side effect-inducing) potential, compounds of formula (I) of the present invention are highly superior to the reference drugs olanzapine and risperidone both in absolute (MED) and relative (TI) terms. Since olanzapine and risperidone show equal binding affinity to the $D_3$ and $D_2$ dopamine receptors (see Table 1) whereas compounds of formula (I) of the present invention preferably bind to the $D_3$ receptor (their $D_3$ affinity is 5 to 50 fold higher than the $D_2$ affinity) in such a way that they have high or very high affinity to dopamine $D_3$ receptors and moderate to high affinity to dopamine $D_2$ receptors, the results of Table 2 also demonstrate that such particular combination of $D_3$ and $D_2$ affinities indeed result in preservation of the beneficial antipsychotic action with simultaneous elimination of the disadvantageous extrapyramidal side-effect (catalepsy).

TABLE 3

Effects of compounds of formula (I) on scopolamine-induced learning disturbance

| Compound | Dose (mg/kg) | % inhibition[a] |
|---|---|---|
| 1 | 0.1 | 36 |
|  | 0.2 | 58 |
|  | 0.4 | 61 |
|  | 0.8 | 44 |
| 8 | 0.025 | 38 |
|  | 0.05 | 65 |
|  | 1 | 31 |
| Olanzapine | 1 | −12 |
|  | 3 | −49 |
| Risperidone | 0.5 | −15 |

[a] negative values mean further impairment in learning performance

Data in Table 3 show that compounds of formula (I) of the present invention do exert cognitive enhancing effect (as evidenced by the considerable inhibition of the learning disrupting effect of scopolamine) in contrast to olanzapine and risperidone which further impaired rather than improved the learning performance of scopolamine treated animals. These findings demonstrate the beneficial effect of the very high to high $D_3$ receptor affinity characteristic for the compounds of formula (I) of the present invention and also point to the importance of the particular 5 to 50-fold $D_3/D_2$ selectivity ratio possessed by these compounds. In the case of risperidone and olanzapine, compounds which showed equal affinity to the $D_3$ and $D_2$ receptors, the deleterious effect of $D_2$

We claim:
1. A compound of formula (I):

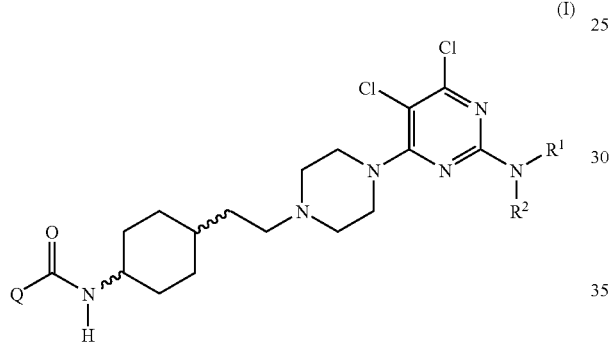

wherein
Q represents $C_{1-4}$ alkyl, —$NR^3R^4$, phenyl, optionally substituted phenyl, 1-pyrrolidinyl, 1-piperidinyl, 4-$R^5$-piperazin-1-yl or 4-morpholinyl group,
$R^1$ represents hydrogen or $C_{1-4}$ alkyl group;
$R^2$ represents hydrogen or $C_{1-4}$ alkyl group;
$R^3$ represents hydrogen, $C_{1-4}$ alkyl group, phenyl or optionally substituted phenyl;
$R^4$ represents hydrogen, $C_{1-4}$ alkyl group, phenyl or optionally substituted phenyl;
$R^5$ represents hydrogen or $C_{1-4}$ alkyl group;
and/or geometric isomers and/or stereoisomers and/or diastereomers and/or salts thereof.

2. The compound of claim 1, wherein
Q represents $C_{1-4}$ alkyl, —$NR^3R^4$ or 4-morpholinyl group,
$R^1$ represents hydrogen atom or $C_{1-4}$ alkyl group;
$R^2$ represents hydrogen atom or $C_{1-4}$ alkyl group;
$R^3$ represents hydrogen atom or $C_{1-4}$ alkyl group; and
$R^4$ represents hydrogen atom or $C_{1-4}$ alkyl group.

3. A compound selected from:
trans-N-(4-{2-[4-(5,6-dichloro-2-methylamino-pyrimidin-4-yl)-piperazin-1-yl]-ethyl]-cyclohexyl}-acetamide,
trans-(4-{2-[4-(5,6-dichloro-2-methylamino-pyrimidin-4-yl)-piperazin-1-yl]-ethyl}-cyclohexyl)-urea,
trans-morpholine-4-carboxylic acid (4-{2-[4-(5,6-dichloro-2-ethylamino-pyrimidin-4-yl)-piperazin-1-yl]-ethyl}-cyclohexyl)-amide,
trans-(4-{2-[4-(5,6-dichloro-2-ethylamino-pyrimidin-4-yl)-piperazin-1-yl]-ethyl}-cyclohexyl)-urea,
trans-N-(4-{2-[4-(5,6-dichloro-2-dimethylamino-pyrimidin-4-yl)-piperazin-1-yl]-ethyl}-cyclohexyl)-acetamide,
trans-N-(4-{2-[4-(5,6-dichloro-2-ethylamino-pyrimidin-4-yl)-piperazin-1-yl]-ethyl}-cyclohexyl)-acetamide,
trans-morpholine-4-carboxylic acid (4-{2-[4-(5,6-dichloro-2-methylamino-pyrimidin-4-yl)-piperazin-1-yl]-ethyl}-cyclohexyl)-amide,
trans-3-(4-{2-[4-(5,6-dichloro-2-methylamino-pyrimidin-4-yl)-piperazin-1-yl]-ethyl}-cyclohexyl-1,1-dimethyl-urea,
trans-3-(4-{2-[4-(5,6-dichloro-2-ethyl-amino-pyrimidin-4-yl)-piperazin-1-yl]-ethyl}-cyclohexyl}-1,1-dimethyl-urea,
trans-1-(4-{2-[4-(5,6-dichloro-2-methylamino-pyrimidin-4-yl)-piperazin-1-yl]-ethyl}-cyclohexyl)-3-ethyl-urea,
trans-N-(4-{2-[4-(5,6-dichloro-2-methylamino-pyrimidin-4-yl)-piperazin-1-yl]-ethyl}-cyclohexyl-propionamide,
trans-N-(4-{2-[4-(2-amino-5,6-dichloro-pyrimidin-4-yl)-piperazin-1-yl]-ethyl}-cyclohexyl)-acetamide,
trans-1-(4-{2-[4-(5,6-dichloro-2-methylamino-pyrimidin-4-yl)-piperazin-1-yl]-ethyl}-cyclohexyl)-3-methyl-urea,
trans-N-(4-{2-[4-(5,6-dichloro-2-methylamino-pyrimidin-4-yl)-piperazin-1-yl]-ethyl}-cyclohexyl)-benzamide,
trans-3-bromo-N-(4-{2-[4-(5,6-dichloro-2-methylamino-pyrimidin-4-yl)-piperazin-1-yl]-ethyl}-cyclohexyl)-benzamide,
and/or geometric isomers and/or stereoisomers and/or diastereomers and/or salts thereof.

4. A compound of formula (III):

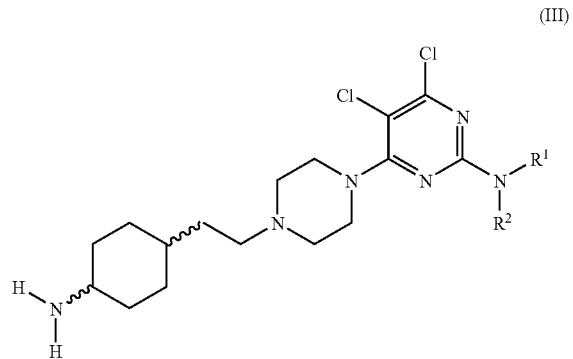

wherein
$R^1$ represents hydrogen or $C_{1-4}$ alkyl group, and
$R^2$ represents hydrogen or $C_{1-4}$ alkyl group and/or geometric isomers and/or stereoisomers and/or diastereomers and/or salts thereof.

5. A process for preparing a compound of formula (I):

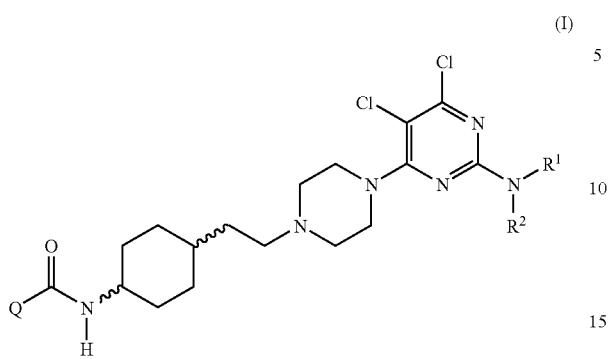

(I)

and/or geometric isomers and/or stereoisomers and/or diastereomers and/or salts thereof,
wherein
Q represents $C_{1-4}$ alkyl, —$NR^3R^4$, phenyl, optionally substituted phenyl, 1-pyrrolidinyl, 1-piperidinyl, 4-$R^5$-piperazin-1-yl or 4-morpholinyl group,
$R^1$ represents hydrogen or $C_{1-4}$ alkyl group,
$R^2$ represents hydrogen or $C_{1-4}$ alkyl group,
$R^3$ represents hydrogen, $C_{1-4}$ alkyl group, phenyl or optionally substituted phenyl,
$R^4$ represents hydrogen, $C_{1-4}$ alkyl group, phenyl or optionally substituted phenyl,
$R^5$ represents hydrogen or $C_{1-4}$ alkyl group
comprising reacting an acid- or carbamoylchloride of formula (II):

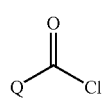

(II)

wherein Q is as described above;
with an amine of formula (III):

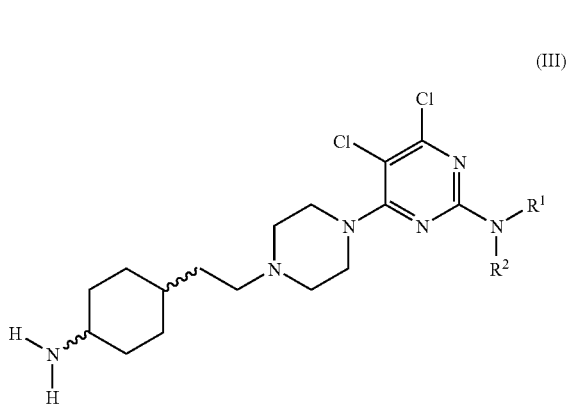

(III)

wherein
$R^1$ represents hydrogen or $C_{1-4}$ alkyl group,
$R^2$ represents hydrogen or $C_{1-4}$ alkyl group,
and, where appropriate, separating the enantiomers and/or diastereomers, and/or cis- and/or trans-isomers of compounds of formula (I), or intermediates thereto, by conventional methods, and optionally thereafter forming salts of the compound of formula (I).

6. A process for preparing a compound of formula (I):

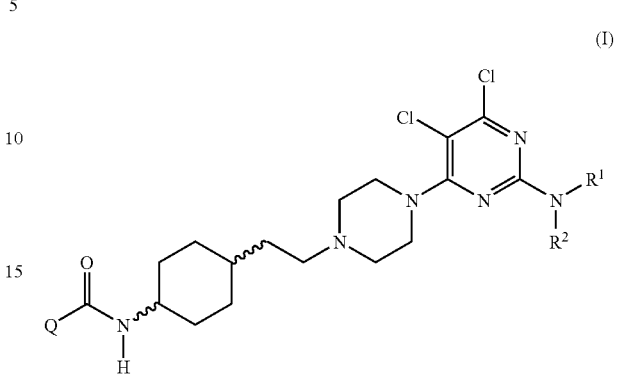

(I)

and/or geometric isomers and/or stereoisomers and/or diastereomers and/or salts thereof,
wherein
Q represents $NR^3R^4$,
$R^1$ represents hydrogen or $C_{1-4}$ alkyl group,
$R^2$ represents hydrogen or $C_{1-4}$ alkyl group,
$R^3$ represents hydrogen, $C_{1-4}$ alkyl group, phenyl or optionally substituted phenyl,
$R^4$ represents hydrogen, $C_{1-4}$ alkyl group, phenyl or optionally substituted phenyl,
comprising reacting an isocyanate of formula (IV):

$R^6$—NCO (IV)

wherein $R^6$ represents $C_{1-4}$ alkyl group, phenyl or optionally substituted phenyl group
with an amine of formula (III):

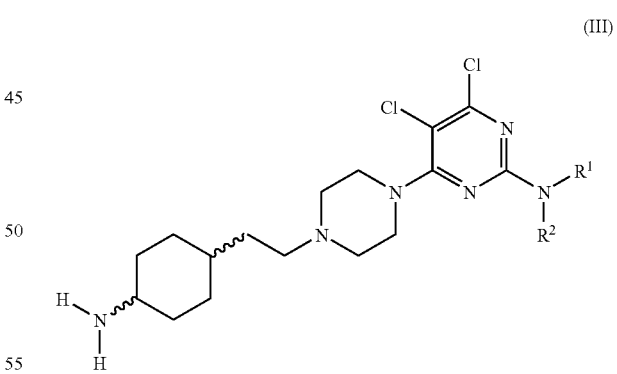

(III)

wherein
$R^1$ represents hydrogen atom or $C_{1-4}$ alkyl group,
$R^2$ represents hydrogen atom or $C_{1-4}$ alkyl group,
and, where appropriate, separating the enantiomers and/or diastereomers, and/or cis- and/or trans-isomers of compounds of formula (I), or intermediates thereto, by conventional methods,
and optionally thereafter forming salts of the compound of formula (I).

7. A process for preparing a compound of formula (I):

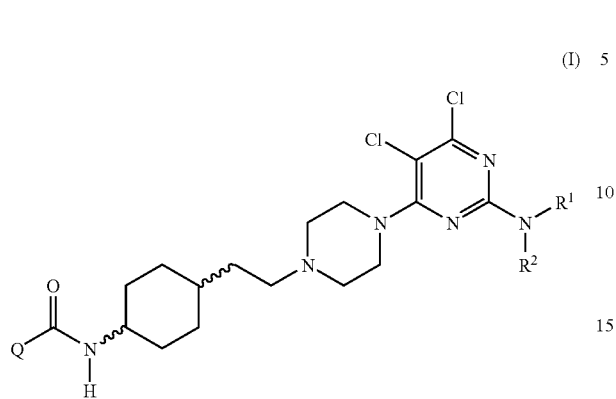

and/or geometric isomers and/or stereoisomers and/or diastereomers and/or salts thereof,
wherein
Q represents amino,
$R^1$ represents hydrogen or $C_{1-4}$ alkyl group,
$R^2$ represents hydrogen or $C_{1-4}$ alkyl group, comprising comprising reacting potassium cyanate or sodium cyanate with an amine of formula (III)

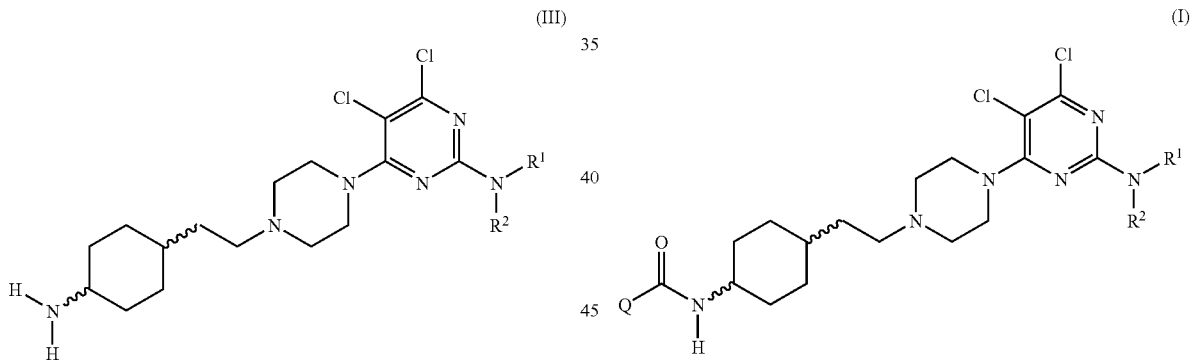

wherein
$R^1$ represents hydrogen or $C_{1-4}$ alkyl group;
$R^2$ represents hydrogen atom or $C_{1-4}$ alkyl group;
and, where appropriate, separating the enantiomers and/or diiastereomers, and/or cis- and/or trans-isomers of compounds of formula (I), or intermediates thereto, by conventional methods,
and optionally thereafter forming salts of the compound of formula (I).

8. A pharmaceutical composition comprising a compound of formula (I)

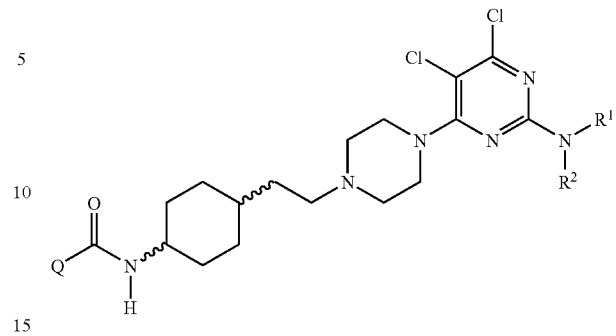

wherein
Q represents $C_{1-4}$ alkyl, —$NR^3R^4$, phenyl, optionally substituted phenyl, 1-pyrrolidinyl, 1-piperidinyl, 4-$R^5$-piperazin-1-yl or 4-morpholinyl group,
$R^1$ represents hydrogen or $C_{1-4}$ alkyl group,
$R^2$ represents hydrogen or $C_{1-4}$ alkyl group,
$R^3$ represents hydrogen, $C_{1-4}$ alkyl group, phenyl or optionally substituted phenyl,
$R^4$ represents hydrogen, $C_{1-4}$ alkyl group, phenyl or optionally substituted phenyl,
$R^5$ represents hydrogen or $C_{1-4}$ alkyl group
and/or geometric isomers and/or stereoisomers and/or diastereomers and/or salts thereof and one or more physiologically acceptable carrier(s).

9. A method of treating Parkinson's disease which comprises administering to a subject in need thereof an effective amount of a compound of formula (I)

wherein
Q represents $C_{1-4}$ alkyl, —$NR^3R^4$, phenyl, optionally substituted phenyl, 1-pyrrolidinyl, 1-piperidinyl, 4-$R^5$-piperazin-1-yl or 4-morpholinyl group,
$R^1$ represents hydrogen or $C_{1-4}$ alkyl group,
$R^2$ represents hydrogen or $C_{1-4}$ alkyl group,
$R^3$ represents hydrogen, $C_{1-4}$ alkyl group, phenyl or optionally substituted phenyl,
$R^4$ represents hydrogen, $C_{1-4}$ alkyl group, phenyl or optionally substituted phenyl,
$R^5$ represents hydrogen or $C_{1-4}$ alkyl group
and/or geometric isomers and/or stereoisomers and/or diastereomers and/or salts thereof.

* * * * *

UNITED STATES PATENT AND TRADEMARK OFFICE
CERTIFICATE OF CORRECTION

PATENT NO.       : 7,875,610 B2
APPLICATION NO.  : 12/327180
DATED            : January 25, 2011
INVENTOR(S)      : Szalai et al.

It is certified that error appears in the above-identified patent and that said Letters Patent is hereby corrected as shown below:

Title Page, Item (56) References Cited, Other Publications, Vippagunta et al. reference, please delete "Cyrstalline" and insert --Crystalline-- therefor;

Column 25, line 27 (Claim 7), after "group" please delete "comprising";

Column 25, line 55 (Claim 7), please delete "diiastercomers" and insert --diastercomers-- therefor.

Signed and Sealed this
Sixteenth Day of August, 2011

David J. Kappos
*Director of the United States Patent and Trademark Office*